United States Patent
Snow et al.

(10) Patent No.: US 7,217,245 B1
(45) Date of Patent: May 15, 2007

(54) NONINVASIVE METHODS FOR DETECTING ABNORMALITIES IN A SUBJECT SUCH AS DISEASE OR DYSFUNCTION

(75) Inventors: Brent W. Snow, Salt Lake City, UT (US); Patrick C. Cartwright, Salt Lake City, UT (US); John T. Mansfield, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/959,030

(22) PCT Filed: Apr. 14, 2000

(86) PCT No.: PCT/US00/10224

§ 371 (c)(1),
(2), (4) Date: Feb. 13, 2002

(87) PCT Pub. No.: WO00/62659

PCT Pub. Date: Oct. 26, 2000

Related U.S. Application Data

(60) Provisional application No. 60/129,457, filed on Apr. 15, 1999, provisional application No. 60/128,461, filed on Apr. 15, 1999.

(51) Int. Cl.
*A61B 5/00* (2006.01)

(52) U.S. Cl. .................. 600/549; 601/2; 600/407; 600/412

(58) Field of Classification Search ............... 600/343, 600/350, 474, 475, 549, 407, 412, 419, 437, 600/438, 420, 412 X; 607/100–102; 128/897, 128/898; 601/2, 3, 2 X, 4
See application file for complete search history.

(56) References Cited

U.S. PATENT DOCUMENTS

| | | | | |
|---|---|---|---|---|
| 3,581,570 A | * | 6/1971 | Wortz | 600/549 |
| 4,140,130 A | | 2/1979 | Storm, III | |
| 4,557,272 A | * | 12/1985 | Carr | 600/549 |
| 4,647,281 A | * | 3/1987 | Carr | 600/549 |
| 4,798,215 A | * | 1/1989 | Turner | 607/102 |
| 5,370,121 A | * | 12/1994 | Reichenberger et al. | 600/438 |
| 5,496,271 A | | 3/1996 | Burton et al. | |
| 5,503,150 A | * | 4/1996 | Evans | 607/102 |
| 5,660,836 A | * | 8/1997 | Knowlton | 424/400 |
| 5,797,398 A | * | 8/1998 | Bowman | 600/549 |
| 5,833,625 A | * | 11/1998 | Essen-Moller | 600/547 |
| 5,913,886 A | * | 6/1999 | Soloman | 607/108 |
| 5,954,668 A | * | 9/1999 | Uber et al. | 600/549 |
| 6,245,094 B1 | * | 6/2001 | Pompei | 607/104 |

* cited by examiner

*Primary Examiner*—Max F. Hindenberg
*Assistant Examiner*—Jonathan Foreman
(74) *Attorney, Agent, or Firm*—Clayton, Howarth & Cannon, P.C.

(57) ABSTRACT

The systems, methods and apparatus of the present invention comprise noninvasive methods of measuring temperature changes and rates of temperature change in selected body tissues and fluids as a result of absorption and/or dissipation of externally applied heat for the purpose of detecting and monitoring disease or dysfunction, and for preparing diagnostic images of the tissues and related areas from such measurements. Some embodiments of the present invention monitor temperatures of heated tissues directly while other embodiments may measure temperatures of tissues which are heated through flow of heated fluid therethrough.

12 Claims, No Drawings

NONINVASIVE METHODS FOR DETECTING ABNORMALITIES IN A SUBJECT SUCH AS DISEASE OR DYSFUNCTION

CROSS-REFERENCE TO RELATED APPLICATIONS

This application is the National Stage of International Application No. PCT/US00/10224, filed Apr. 14, 2000, which claims the benefit of U.S. Provisional Application No. 60/129,457, filed Apr. 15, 1999, and U.S. Provisional Application No. 60/129,461, filed Apr. 15, 1999.

BACKGROUND OF THE INVENTION

1. The Field of the Invention

The present invention relates to a noninvasive method for measuring temperature changes in tissues in a subject during and after heating to detect disease or dysfunction of the tissues, to monitor the progress and/or treatment of such disease or dysfunction and to detect the flow of body fluids. In particular embodiments, such measurements may be used to prepare images of the tissues, fluid pathways and related matter.

2. Background of the Invention

Body tissues, including solid tissues such as organs, for example the kidney, liver and spleen, are vulnerable to a number of diseases, such as cancer, inflammation, scarring and deleterious changes in functioning that cause a change in physical characteristics of the tissue. For example, inflammation causes swelling, scarring results in increased density, and alterations in function can create changes in metabolic energy. Such physical changes may also result in changes in the manner in which tissue warms and dissipates applied heat. For example, tissues infiltrated by cancer have been observed to exhibit differential heating characteristics when heat is applied to the tumors (Song, "Blood flow in tumors and normal tissues in hyperthermia," in Hyperthermia in Cancer Therapy (Storm, ed.), GK Hall Medical Publisher, Boston, Mass., pp 187–206 (1983)).

Currently, imaging of solid tissues to detect the presence and extent of diseases such as cancer is conducted using procedures such as fluoroscopy, ultrasound and x-ray radiation. Nuclear magnetic resonance (NMR) has been used to provide temperature images of solid tissues (U.S. Pat. Nos. 4,558,279 and 4,554,925). Each procedure offers advantages and disadvantages, and often more than one procedure is used to complement the other and assess a patient's condition. The measurement of temperature changes has been used to monitor hyperthermia treatments (U.S. Pat. No. 4,638,436).

The warming of tissue in humans using external energy has been previously described, for example using microwave technology in urology to a limited extent for treatment of tumors in adults. (Hornback, *Hyperthermia and Cancer: Human Clinical Trial Experiments Vol. II,* CRC Press, Boca Raton, Fla. (1984)). Radio frequency and electromagnetic radiation have been used to treat tumors. (U.S. Pat. No. 3,991,770 and U.S. Pat. No. 4,140,130). Microwave radiometry has been used to measure body temperatures (U.S. Pat. No. 4,583,869) for diagnosis, for example for tumor detection (see Foster and Cheever, *Bioelectromagnetics* 13:567–579 (1992)).

Various conditions exist in which body fluids, such as urine or blood, improperly flow as a result of disease or dysfunction. For example, vesicoureteral reflux involves movement of urine from the bladder through the ureters to the kidneys contributing to kidney infection, particularly in children. Similarly, gastroesophageal reflux is common in young children and requires nasogastric tubes to be placed to instill x-ray contrast to image whether reflux occurs. Other conditions involve disruptions in blood flow or myocardial function resulting from narrowing of the aorta, blood clots, or malfunction of the enterohepatic circulation or a portion of this system, e.g. the intestine, liver or gall bladder, or disruptions in flow of cerebrospinal fluid. Previously, diagnosis of such conditions has required invasive procedures such as use of catheters or tubes.

In pediatric urology there is a great need to noninvasively measure whether urine from the bladder refluxes to the kidneys. Diagnostic procedures are recommended for all children who have urinary tract infections and for many who suffer from bladder dysfunction causing wetting. Such studies may reveal abnormalities such as urine backflow to the kidney referred to as "reflux." Reflux is critical to diagnose because in its presence the majority of kidney damage during childhood occurs.

Currently two radiologic imaging studies are utilized: voiding cystourethrogram (VCUG) and a nuclear cystogram. A VCUG is performed in humans of all ages by first placing a sterile catheter in the patient's urethra and through the catheter instilling radiopaque contrast, such as Hypaque™, into the bladder under 60 centimeters of gravity pressure. The kidneys and bladder are observed during a bladder filling and emptying cycle using x-rays. The patient has as initial x-ray film taken, then an anterior-posterior film and then films in each lateral oblique. When voiding is initiated, fluoroscopy is utilized, and spot films are taken to document changes during voiding. This process is necessary to evaluate bladder anatomy, function, elimination and vesicoureteral reflux.

An alternative diagnostic study called a nuclear cystogram still requires the ordeal of catheter passage into the urethra and then radioactive particles are instilled into the bladder. Nuclear cystogram is performed after a sterile catheter is placed in the patient's urethra. Radionuclide is instilled into the bladder and the patient is imaged with a gamma camera to evaluate bladder function, elimination and vesicoureteral reflux. The radiation dose is reduced but not eliminated. Moreover, visual images obtained from this study are typically of poor quality.

Although it is the bladder that is invaded by a catheter in these diagnostic procedures, the critical information obtained involves the kidneys and leads to protection from kidney damage. If reflux of urine to the kidney is detected, the diagnostic tests need to be repeated in the same child at regular intervals until the reflux is resolved. Repeat tests heighten the anxiety of the child and the parents.

These examinations have been utilized for years and are very familiar to pediatricians and adult physicians alike. A limitation of VCUG's or nuclear cystograms is availability. These studies are currently performed in hospital radiology departments and generally are not available on a same day basis. It would be advantageous for physicians to be able to carry out a noninvasive procedure to detect organ or tissue dysfunction at the point of care clinic or office.

The majority of the patients undergoing these studies are children and the placement of urethral catheters is an ordeal for the patients and the medical personnel. In addition, VCUG carries risks of urethral damage and urinary tract infection. The need exists for a noninvasive, catheterless, technique for evaluating bladder function—e.g. process of bladder emptying, elimination and vesicoureteral reflux. This is very important in adults with outlet obstruction who empty their bladders poorly. This currently is measured with a postvoid catheter or with ultrasound.

Currently the degree of vesicoureteral reflux is graded on an international scale of 1 to 5. Treatment is based upon the grade given to the reflux to each kidney and either medical management or surgical treatment is chosen. Generally Grades 1 thru 3 are assigned nonsurgical management while Grades 4 and 5 are surgically corrected.

In children, categories of patients who currently undergo VCUG's or nuclear cystograms are: 1) newborns with antenatal hydronephrosis (water-swollen kidneys); 2) patients during childhood who have a urinary tract infection; and 3) patients with enuresis (urinary incontinence) either during the day or night. One out of every 200 babies have antenatal hydronephrosis discovered prior to delivery. Most of these patients will have this kidney dilation confirmed postnatally and require a VCUG along with a renal ultrasound. In male children it may be necessary to continue to perform VCUG's to better visualize the anatomy of the urethra, but in female children and some of the males, a noninvasive study would be indicated.

Approximately 2% of all children at any one time have a urinary tract infection. After the first infection it is currently recommended that patients undergo a VCUG and a renal imaging study. Doctors are sometimes reluctant to order the invasive VCUG until other infections occur. Of the VCUGs performed, approximately one of three patients will have vesicoureteral reflux. The reflux is graded and treatment is assigned on the basis of severity. About three-quarters of the patients are assigned to medical management and are screened with a VCUG each year until their reflux resolves. This averages about three years of waiting before resolution occurs. Patients who undergo surgical correction of their reflux also require a follow-up VCUG to evaluate the success of the procedure. Patients with enuresis either at night or during the day are evaluated with VCUGs on occasion. Since the test is currently invasive it is withheld until the patients are older or unusual symptoms indicate its necessity.

To synthesize these numbers in Group 1, every patient would need a VCUG. In Group 2, all children should have a VCUG and one out of every three would need a VCUG. Group 3 would still have a significant number of studies and if noninvasive technology was available even more studies would be performed. While adults undergo VCUG's less frequently, the procedure is still uncomfortable and simple, relatively inexpensive, noninvasive studies would still be desirable.

The warming of tissue in humans using external energy has been previously described, for example using microwave technology in urology to a limited extent for treatment of tumors in adults. (Hornback, *Hyperthermia and Cancer: Human Clinical Trial Experiments, Vol. II*, CRC Press, Boca Raton, Fla. (1984)). Radio frequency and electromagnetic radiation have been used to treat tumors. (U.S. Pat. No. 3,991,770 and U.S. Pat. No. 4,140,130). Microwave radiometry has been used to measure body temperatures (U.S. Pat. No. 4,583,869) for diagnosis, for example for tumor detection (see Foster and Cheever, *Bioelectromagnetics* 13:567–579 (1992)).

Diagnostic uses of microwave radiometry have also been proposed for a variety of conditions including measurement of blood flow rates in tissues, such as flow of cerebral blood (Gabrielyan et al., in Methods, pp 713–715, Plenum Press, NY (1987)) and changes in lung water content (Iskander et al., *IEEE Trans Microwave Theory Tech MTT* 32:554–556 (1984); U.S. Pat. No. 4,488,559). Gabrielyan et al. heated a part of the brain using microwaves and measured the rate of temperature drop of the tissue using a radiometer to determine the rate of cerebral blood flow. Iskander et al. used radiometry to detect changes in lung water content by measuring emitted microwave radiation.

In these prior known methods externally applied energy was not used to heat tissues, to measure warming or heat dissipation characteristics, for the purpose of detecting and/or monitoring the condition of the tissues within a subject, or to construct images of the tissue from such measurements for diagnostic purposes. Furthermore, externally applied heat was not employed to warm fluid within tissue or organs, in order to follow its flow path and determine the presence of disease or dysfunction within a subject. Thus, there remains a need for noninvasive methods to evaluate the condition of tissues, to determine or monitor the presence of disease and/or dysfunction.

A need also remains for noninvasive methods to track the flow of body fluids, such as urine, from one location within a subject to another, to determine the presence of disease and/or dysfunction and to monitor the progress of the disease and/or medical intervention.

SUMMARY OF THE INVENTION

Accordingly, embodiments of the present invention provide a noninvasive method for determining the flow of bodily fluids in a subject by administering external energy, such as microwave or ultrasound energy, to warm a fluid in the organ or tissue, and then detecting the path of the warmed fluid. The body fluid can be urine, blood, cerebrospinal fluid, bile, lymph, or gastric fluid. A temperature change, i.e. temperature increase, in a location distant from the site of warming of the fluid, indicates that the warmed fluid has passed into the distant location. In one embodiment, urine in the bladder is warmed and the presence of warmed urine in the kidney is detected to determine whether a reflux condition is present. In addition, bladder functioning, i.e. bladder emptying, is determined using the methods of the invention.

In another embodiment, the warmed body fluid is gastrointestinal fluid, and flow into the stomach of the subject from other locations is detected. In another embodiment, the warmed body fluid is blood, and flow from or to the heart is detected. In another embodiment, the body fluid is cerebrospinal fluid, and flow of the fluid to or from the brain, or through the spine, is detected.

In another embodiment, a warmed fluid is introduced into the subject and the flow of the fluid throughout the body of the subject is detected.

Further embodiments of the present invention provide a noninvasive method for determining the condition of tissues by administering external energy such as microwave or ultrasound energy to heat a tissue while measuring the temperature changes and heat dissipation of the tissue and comparing to measurements of temperature changes in normal tissues when heated. Alternatively, heat dissipation after heating may be measured and compared to measurements on a normal or control tissue. Differences in the temperature changes during heating and heat dissipation of the tissue may indicate the presence of disease or dysfunction, and can be used to monitor the progress and/or treatment of the condition. Rates of temperature increase or decrease of heated tissue are also compared with rates of temperature increase or decrease for corresponding normal tissues to detect the presence of disease or dysfunction.

Images may be prepared from these measurements by converting the temperature measurements to visible signals such as colors to display for diagnostic purposes.

DETAILED DESCRIPTION OF THE INVENTION

Embodiments of the present invention provide noninvasive methods for detecting and monitoring the condition of a subject by administering external energy such as microwave or ultrasound to heat selected tissue or fluids and measuring temperature changes of the tissue or fluids during heating and heat dissipation and comparing such changes to measurements for normal tissue or fluids during heating and heat dissipation. These methods are useful, for example, to detect disease or dysfunction or to monitor the progress of a condition in a subject.

Some methods of the present invention rely on the noninvasive heating of selected regions of tissue in a subject using an externally applied energy source, and the non-invasive measurement of the temperature changes throughout the tissue using a temperature sensing device. Any diseased or dysfunctional portions of the tissue will absorb the heat from the external source differently, i.e. exhibit different rates of temperature change, than temperature changes measured in normal tissue during heating. Similarly, diseased tissue will dissipate heat differently than normal tissue. The measurements of temperature changes of the selected regions of tissue in the subject are then compared to measurements obtained for corresponding normal tissue (i.e. non-diseased tissue) from subjects to determine the presence and extent, if any, of diseased or dysfunctional tissue.

Measurements are also taken of the rate of temperature change upon heating or heat dissipation in selected tissue and compared to rates measured in corresponding normal tissue to diagnose the presence and extent of disease or dysfunction.

The temperature measurements of heat absorption or dissipation of the selected tissue or the rate of temperature change may be used to construct an image, such as a color image, of the tissue to provide a rapid diagnostic test for determining deleterious changes in anatomy and/or function of the selected tissue. The image is produced, for example, and not by way of limitation, by integrating the temperature data with the temperature sensor location (direction) and the depth of the temperature signal. For this application, multiple sensors are preferred to provide the image. The data are assigned colors which are then displayed as an image on a device for viewing. The image may be generated and displayed essentially simultaneously during temperature measurements of the selected tissue.

The external applied energy for heating selected tissues or fluids in the methods of the present invention may be any form of energy capable of safely heating human tissue, including microwave energy or ultrasound. Devices for applying microwave energy to heat using 600 to 1500 MHz electromagnetic power are known (e.g. Chou, *Bioelectromagnetics* 13:582–597 (1992); BSD Systems, Salt Lake City, Utah) and may be modified as needed to apply energy of the desired frequency and penetration. Ultrasound heating systems for use in the invention can be readily assembled using ultrasound crystals of a range of emitting frequencies from 500 Kilohertz to 12 MHz (Channel Industries, Santa Barbara, Calif.) and a suitable amplifier providing from 0 to 100 watts to heat tissues within the subject at different depths. The crystals are positioned manually or by computer to focus the applied heat as desired.

To apply the external energy to warm the fluid, the device is positioned on the skin of the subject above the tissue to be warmed or above the organ or tissue containing the fluid to be warmed, and is activated for the selected time sufficient to warm the fluid or tissue, but not to the point that the warmed fluid or tissue would cause pain or damage, typically less than 45° C. Ultrasound detection may be used to assist in positioning of the heating device over the space containing the fluid to be warmed. External energy is typically applied for less than 20 minutes to uniformly heat the fluid, for example to heat a bladder to warm the urine contained within.

The energy sensor for measuring temperatures of the tissue may be a radiometer (RES Ltd., Moscow, Russia). For example, microwave radiometers can measure subsurface temperatures at depths of millimeters to centimeters. Temperature changes of at least 0.3° C. can be detected.

Further embodiments of the present invention provide noninvasive methods for detecting the flow of fluids in organs and tissues in a subject by administering external energy such as microwave or ultrasound. The method is useful, for example, to detect vesicoureteral reflux in subjects, and to quantify the amount of reflux to the kidney, and to study characteristics of emptying the bladder to detect disease or dysfunction. The method relies on the non-invasive warming of a bodily fluid in a selected space, for example urine in a bladder or cerebrospinal fluid in the brain and/or spinal column, using an externally applied energy source, and the non-invasive measurement of a temperature change in the space into a distal space through which the warmed fluid passes or into which the warmed fluid passes and collects (e.g. kidney) resulting from the inflow of the warmed fluid.

The methods of the invention may be used to detect and characterize the flow of various fluids in the body including, but not limited to, urine, blood, cerebrospinal fluid, bile and gastric fluid.

After a sufficient period of time, for example 5 to 10 minutes, the temperature change in tissues or organs distal to the point of application of energy resulting from the presence of the warmed fluid is detected and measured by a non-invasive device such as a radiometer. Microwave radiometers (e.g. from RES Ltd., Moscow Russia operating in the 1100 to 1200 MHz range) can measure subsurface temperatures at depths of millimeters to centimeters. For example, after heating the urine in a bladder, the detecting device is positioned on the skin over the kidney to detect the presence of any warmed fluid indicating reflux. A temperature change of at least 0.3° C. stable for at least 1 minute detected in the kidney indicates that the warmed fluid has traveled into the kidney suggesting a reflux condition exists. The amount of urine present in the kidney is used to establish the severity of reflux, typically stated as a value from 1 to 5 (see Walker, *Vesicoureteral Reflux and Urinary Tract Infection in Children in Adult and Pediatric Urology*, $3^{rd}$ Ed., Mosby, St. Louis, Mo. 1996).

The amount of liquid refluxing to the distal location can be determined from the amount of temperature change detected in the distal location. For example, a measured temperature change in a given area, e.g. kidney, can be used to calculate the volume of fluid needed to cause the temperature change.

In addition, bladder functioning in terms of characteristics of bladder emptying can be determined using the methods of the invention. For example, the rate (volume change/time) of bladder emptying can be determined from the rate of temperature decrease in the bladder as the warmed fluid exits during voiding, and is then compared to "normal" flow rates of emptying that have been established for specific age groups by the medical profession.

In another embodiment, gastrointestinal fluids in the stomach are warmed to less than 45° C. and the flow of the warmed fluids is followed to detect possible reflux of such fluids into the esophagus and duodenum to detect antegrade and retrograde flow (gastroesophageal reflux) by detecting temperature changes in the esophagus and/or duodenum. In addition, bile acid is warmed in the gall bladder to detect bile acid reflux from the duodenum to the stomach to diagnose duodenal gastric reflux, and to detect malfunction of the enterohepatic circulation or a portion of the circulation, e.g. the intestine, liver or gall bladder.

In yet another embodiment, blood is warmed in the heart, and the flow of the warmed blood flow is followed through the vascular tree to evaluate adequacy of blood flow through the body and to detect any obstructions of blood vessels by detecting temperature changes at various positions in the circulatory system.

In still another embodiment, cerebrospinal fluid is warmed in the spinal column and/or cranial vault and the flow of fluid is followed throughout to detect any problems in the cerebrospinal anatomy and extent of any disease processes by detecting temperature changes in the spinal column and cranium.

In another embodiment, a warm liquid is introduced into the subject and the path of the liquid is followed, for example by detecting temperature changes in the stomach and esophagus.

The methods of the invention eliminate the need for invasive procedures to detect diseased or dysfunctional tissue while also reducing risk to patients. The methods of the invention do not require a catheter, nasogastric tube or other similar device or invasive procedure which cause discomfort to the subject and can contribute to tissue injury or infection. In the case of use on the bladder, the chances of urethral injury and urinary tract infection following imaging procedures are eliminated. In addition, the methods eliminate the need for examination using ionizing x-ray radiation, reducing risk to patients.

The following examples are presented to demonstrate methods of the present invention and to assist one of ordinary skill in using the same. These examples are not intended in any way to otherwise limit the scope of the disclosure or the protection granted hereon.

EXAMPLE 1

Detecting Disease or Dysfunction of the Kidney

A subject is screened to detect disease or dysfunction of kidney tissues using the methods of the invention as follows. A temperature sensing radiometer is used to determine the "before" temperature throughout the kidney. A portable microwave or ultrasound capable of penetrating to at least 10 cm is placed on the skin over the kidney of a subject and the device is activated to direct 100 to 200 watts (W) (variable power) at 27 to 1500 MHz to uniformly heat the kidney in order to elevate the temperature of the kidney from its existing temperature to between 37° C. and 45° C. The temperature increases throughout the kidney are sensed using a radiometer for 1 to 20 minutes during heating, by placing the radiometer on the skin of the subject over the kidney. Multiple heat sensing devices, e.g. radiometers, may be used for the measurements throughout the kidney.

The measurements obtained during heating are compared to temperature changes measured in tissue in kidneys in normal subjects that have undergone the same non-invasive heating and temperature measuring procedures. This comparison establishes differences in "test" kidney tissue to determine the presence of disease or dysfunction that alters the tissue's ability to absorb heat.

Similarly, after a sufficient period of time after the heating, for example 20 minutes, the temperature changes throughout the kidney during heat dissipation are measured by the radiometer, or using multiple radiometers. Again, these measurements are compared to temperature changes measured after heating of tissue in "normal" kidneys to detect disease or dysfunction that has altered the kidney tissue's ability to dissipate heat. Rates of heating or dissipation may also be determined and compared to rates of heating or dissipation of normal kidney tissue.

Significant differences in the patterns of heating and heat dissipation in a subject kidney reveal the presence and extent of disease or dysfunction.

The temperature data can be converted to images by assigning color values to increases or decreases and the images obtained compared to images for temperature changes in tissue of normal kidneys.

Using the methods of the invention, differences in heat absorption and heat dissipation between the subject's kidney and values pre-determined for normal kidneys provide information to the medical practitioner regarding the presence and extent of disease, as well as disease progression and the success of medical intervention.

EXAMPLE 2

Detection of Urine Flow in a Subject by Measuring Temperature Changes to Detect Vesicoureteral Reflux from the Bladder A subject is administered fluids and tested using the following procedures to determine whether the subject suffers from vesicoureteral reflux. A radiometer is used to determine the "before" temperature of the kidney. A portable microwave or ultrasound capable of penetrating to at least 10 cm is placed on the skin over the bladder of a subject and the device is activated to direct 100 to 200 watts (W) (variable power) at 27 to 1500 MHz to heat the urine in the bladder to 42° C. stable for 1 minute. The subject then voids urine from the bladder, and after 1 minute a radiometer is placed on the skin of the subject over the kidney and the temperature of the kidney is measured to determine whether any increase is detected (the "after" temperature) indicating reflux of urine from the bladder to the kidney. The temperature changes registered in the kidney are a direct result of the amount of thermal energy the warmed urine brings to the kidney as a result of reflux.

Using these methods, the temperature deflection of at least 0.3° C. in the kidney due to the presence of warmed fluid indicates the presence of refluxed urine. 10 to 20 minutes after the subject voids, if no temperature change is detected in the kidney, a diagnosis of no reflux can be made.

Various publications are cited herein which are hereby incorporated by reference in their entirety.

As will be apparent to those skilled in the art in which the invention is addressed, the present invention may be embodied in forms other than those specifically disclosed above without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the example contained in the foregoing description.

What is claimed is:

1. A noninvasive method for detecting the flow of body fluids in a subject comprising:

noninvasively warming urine in the subject's bladder with an external energy source of ultrasound energy; and noninvasively detecting the flow of said warmed urine from said bladder to the subject's kidney by measuring a temperature change in said kidney.

2. The method of claim 1 wherein said detecting comprises determining an increase in temperature in said kidney indicative of the presence of said warmed urine.

3. The method of claim 1 further comprising determining a rate of temperature change in said kidney.

4. A noninvasive method for detecting the flow of body fluids in a subject comprising:

noninvasively warming gastrointestinal fluid in the subject's stomach with an external energy source of ultrasound energy; and noninvasively detecting the flow of said warmed gastointestinal fluid from said stomach to the subject's esophagus or duodenum by measuring a temperature change in said esophagus or duodenum.

5. The method of claim 4 wherein said detecting comprises determining an increase in temperature in said esophagus or duodenum indicative of the presence of said warmed gastointestinal fluid.

6. The method of claim 4 further comprising determining a rate of temperature change in said esophagus or duodenum.

7. A noninvasive method for detecting the flow of body fluids in a subject comprising:

noninvasively warming blood in the subject's heart with an external energy source of ultrasound energy; and noninvasively detecting the flow of said warmed blood from said heart to the subject's vascular tree by measuring a temperature change in said vascular tree.

8. The method of claim 7 wherein said detecting comprises determining an increase in temperature in said vascular tree indicative of the presence of said warmed blood.

9. The method of claim 7 further comprising determining a rate of temperature change in said vascular tree.

10. A noninvasive method for detecting the flow of body fluids in a subject comprising:

noninvasively warming cerebrospinal fluid in the subject's spinal column or cranial vault with an external energy source of ultrasound energy; and noninvasively detecting the flow of said warmed cerebrospinal fluid in said spinal column or cranial vault by measuring a temperature change in said spinal column or cranial vault.

11. The method of claim 10 wherein said detecting comprises determining an increase in temperature in said spinal column or cranial vault indicative of the presence of said warmed cerebrospinal fluid.

12. The method of claim 10 further comprising determining a rate of temperature change in said spinal column or cranial vault.

\* \* \* \* \*